United States Patent [19]

Diveley

[11] 3,950,366

[45] Apr. 13, 1976

[54] METAL SALTS OF 1,1,5,5-TETRASUBSTITUTED DITHIOBIURETS

[75] Inventor: William R. Diveley, Wilmington, Del.

[73] Assignee: Hercules Incorporated, Wilmington, Del.

[22] Filed: May 10, 1973

[21] Appl. No.: 359,164

[52] U.S. Cl............ 260/429.9; 260/239 E; 260/242; 260/247; 260/247.1 T; 260/269; 260/270 PD; 260/293.73; 260/293.85; 260/313.1; 260/429 R; 260/429 K; 260/429.7; 260/431; 260/433; 260/438.1; 260/552 R; 424/248; 424/267; 424/274; 424/322

[51] Int. Cl.$^2$.......................................... C07F 3/00

[58] Field of Search......... 260/429 K, 429 R, 429.9, 260/438.1, 552 R, 429.7, 431, 433

[56] References Cited

UNITED STATES PATENTS

| | | | |
|---|---|---|---|
| 2,410,862 | 11/1946 | Bousquet et al................... | 260/552 |
| 3,149,338 | 9/1934 | Habicht et al............. | 260/552 R X |
| 3,166,564 | 1/1965 | Diveley....................... | 260/552 R X |
| 3,686,244 | 8/1972 | Marks......................... | 260/429.9 X |
| 3,799,960 | 3/1974 | Marks.......................... | 260/429.9 X |

OTHER PUBLICATIONS

Chemical Abstracts, Vol. 75, 109156e (1971).
Chemical Abstracts, Vol. 52, 1239g (1958).
Borkovec Insect Chemosterilants, Interscience Pub. John Wiley and Sons, N.Y. pp. 60–62 (1966).

Primary Examiner—Helen M. S. Sneed

[57] ABSTRACT

Disclosed are novel metal salts of 1,1,5,5-tetrasubstituted dithiobiurets of the formula

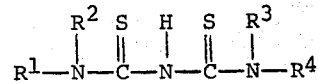

in which $R^1$, $R^2$, $R^3$ and $R^4$, when taken independently of each other are selected from the group consisting of $C_1$-$C_{18}$ alkyl, $C_6$-$C_{12}$ aryl, $C_3$-$C_{12}$ cycloalkyl, and these radicals substituted by at least one member of the group consisting of hydroxyl, $C_1$-$C_4$ alkyl, $C_1$-$C_8$ acyl, halo and nitro, and $R^1$ and $R^2$, when taken together along with the nitrogen to which they are bonded, and $R_3$ and $R^4$ when taken together with the nitrogen to which they are bonded, are selected from the group consisting of N-morpholinyl, N-piperidyl, N-pyrrolidyl and N-aziridinyl. The compounds are useful as population control agents.

7 Claims, No Drawings

METAL SALTS OF 1,1,5,5-TETRASUBSTITUTED DITHIOBIURETS

This invention is in the chemical arts. It relates to the chemistry of thioureas and particularly of dithiobiurets.

Dithiobiurets of the formula:

in which R and R' are certain substituted amino groups, and two processes for making them are disclosed in the U.S. Pat. No. 3,166,564, to Diveley. These compounds which have several useful biological properties are not very stable and tend to oxidize fairly rapidly. This is especially true of 1,1,5,5-tetramethyldithiobiuret and 1,1,5,5-tetraethyldithiobiuret. The dithiobiurets are also relatively insoluble in water.

This invention is based on the discovery that metallic ions react with these dithiobiurets to form salts, many of which are highly stable. These metal salts have many of the same, if not more, biological properties that make them useful.

In summary, this invention comprises a group of compounds which are metal salts of 1,1,5,5-tetrasubstituted dithiobiurets of the formula:

in which $R^1$, $R^2$, $R^3$ and $R^4$, when taken independently of each other are selected from the group consisting of $C_1$-$C_{18}$ alkyl, $C_6$-$C_{12}$ aryl, $C_3$-$C_{12}$ cycloalkyl, and these radicals substituted by at least one member of the group consisting of hydroxyl, $C_1$-$C_4$ alkyl, $C_1$-$C_8$ acyl, halo and nitro, and $R^1$ and $R^2$, when taken together along with the nitrogen to which they are bonded, and $R^3$ and $R^4$ when taken together with the nitrogen to which they are bonded, are selected from the group consisting of N-morpholinyl, N-piperidyl, N-pyrrolidyl and N-aziridinyl. In some embodiments $R^1$, $R^2$, $R^3$ and $R^4$ are the same. In other embodiments one or more of them are different. Examples of metals are the light metals, such as the alkali metals (sodium, potassium, etc.) and the alkaline earth metals (calcium, barium, etc.) and the heavy metals such as zinc, cadmium, tin, mercury, copper, nickel, chromium, iron, silver, manganese, cobalt and the like. Examples of $C_1$-$C_8$ alkyl are both straight and branched chain alkyls such as methyl, ethyl, propyl, isopropyl, n-butyl, sec-butyl, t-butyl, and the like. Examples of $C_{6-C12}$ aryl include phenyl, tolyl, naphthyl, and the like. Examples of $C_3$-$C_{12}$ cycloalkyl include cyclopropyl, cyclobutyl, cyclopentyl, cyclohexyl, and the like. Examples of $C_1$-$C_4$ alkyl include methyl, ethyl, propyl, isopropyl, t-butyl, and the like. Examples of $C_1$-$C_8$ acyl include formyl, acetyl, butyryl, and the like. Specific embodiments of halo are fluoro, chloro, bromo and iodo. Examples of the compounds of this invention include: sodium salt of 1,1,5,5-tetramethyldithiobiuret; sodium salt of 1,3-bis(N-morpholino)-1,3-dithiono-2-azapropane; zinc (II) salt of 1,1,5,5-tetramethyldithiobiuret; nickel (II) salt of 1,1,5,5-tetramethyldithiobiuret; tin (II) salt of 1,1,5,5-tetramethyldithiobiuret; copper (I) salt of 1,1,5,5-tetramethyldithiobiuret; mercury (II) salt of 1,1,5,5-tetramethyldithiobiuret; nickel (II) salt of 1,1,5,5-tetraethyldithiobiuret; and zinc (II) salt of 1,1,5,5-tetraethyldithiobiuret.

NMR spectra, ultraviolet spectra and polarographic data indicate that some of the salts of this invention are ionic salts while others are chelated salts which are more commonly called chelates. In general, the light metal salts are ionic and the heavy metal salts are chelated, although some of the salts are of intermediate character.

The ionic salts of this invention can be represented by the following formula I:

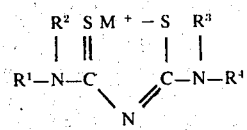

The chelated salts of this invention can be represented by the following formula II in the case of the salts of metal in the monovalent condition or oxidation state:

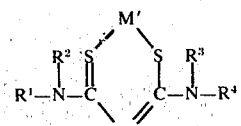

and by formula III in the case of metals in the divalent condition or oxidation state:

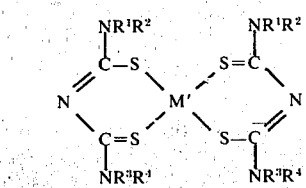

In these formulas $R^1$, $R^2$, $R^3$ and $R^4$ are as defined above, M is a light metal selected from the group consisting of alkali metals and alkaline earth metals with the exception of beryllium and magnesium and M' is selected from the group consisting of the heavy metals, beryllium and magnesium.

In general, the light metal salts exhibit all of the properties normally associated with ionic salts. In general, they are crystalline solids at 20–25°C. and are highly soluble in water, but relatively insoluble in organic solvents such as hexane, benzene, methylene chloride and the like.

In general, the heavy metal salts and the beryllium and magnesium salts of 1,1,5,5-tetrasubstituted dithiobiurets exhibit properties typical of chelated metal salts. Many of the chelated salts are exceptionally stable compounds. In general, they are crystalline solids at 20°–25°C. and are insoluble in water but soluble in solvents such as benzene and the like and chloroform and the like.

The compounds of this invention when applied to plants and administered to animals have a number of advantageous effects. Some of the compounds defoliate plants. Some temporarily sterilize arthropods. Some inhibit metamorphosis of insects and acarids. Some affect the size and function of certain glands in animals.

Some temporarily sterilize animals. In the case of egg-laying animals, some of the compounds suppress egg-laying and eggs that are laid do not hatch. Some of the compounds terminate pregnancy when administered to pregnant mammals. All of the compounds of this invention have one or more of these biological properties.

Each of the compounds of this invention is derived from the corresponding dithiobiuret. Two procedures for making the corresponding dithiobiurets are disclosed in the U.S. Pat. No. 3,166,564, to Diveley. Briefly, the two procedures for preparing the dithiobiurets can be illustrated by the following reaction A:

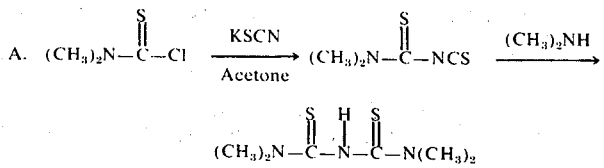

and by the reaction B:

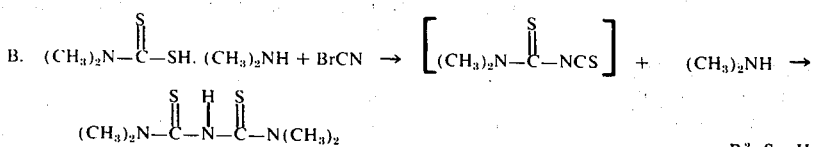

The dithiobiuret salts of this invention are prepared by reacting a compound of the corresponding metal with the corresponding 1,1,5,5-tetrasubstituted dithiobiuret. The corresponding dithiobiuret can be made in situ and, without isolation, reacted directly with the metal compound, or the dithiobiuret can be isolated and then reacted with the metal compound.

Each of the ionic light metal salts of 1,1,5,5-tetrasubstituted dithiobiurets is made by reacting the dithiobiuret with the corresponding light metal alcoholate. The reaction can be represented by the following equation:

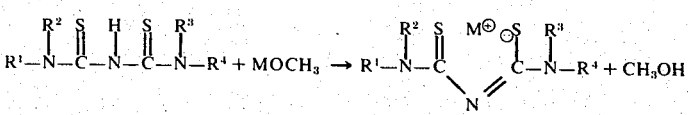

The reaction is preferably carried out in an inert liquid reaction medium such as, for example, methanol and the like. The temperature at which the reaction takes place is not critical, but the reaction proceeds more rapidly at higher temperatures. It is preferred to conduct the reaction at temperatures in the range from about 20°C. to about 30°C. The reaction is generally carried out at atmospheric pressure. However, superatmospheric and subatmospheric pressures are within the broader concepts of this invention.

Each of the heavy metal salts of 1,1,5,5-tetrasubstituted dithiobiurets is made by reacting a salt of the heavy metal with the dithiobiuret. The preparation of chelated salts in the case of salts of metals in the divalent condition or oxidation state can be illustrated by the following equation:

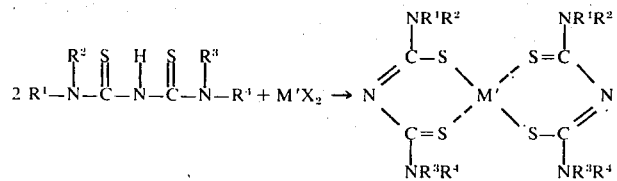

where X is an anion of an acid, HX.

In the case where the metal ion is a sufficiently strong oxidizing agent to oxidize the dithiobiuret as taught in U.S. Pat. No. 3,166,564, for example, the copper (II) ion, the reaction can be illustrated by the following equation:

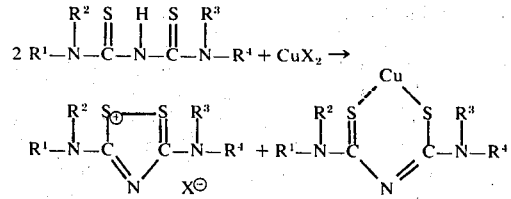

In each case the reaction of the metal salt with the dithiobiuret preferably is carried out in an inert liquid reaction medium, for example, acetone, ethanol and the like. The temperature at which the reaction takes place is not critical, but the reaction proceeds more rapidly at higher temperatures. It is preferred to conduct the reaction at temperatures in the range from about 20° to about 30°C. The reaction is generally carried out at atmospheric pressure. However, superatmospheric and subatmospheric pressures are within the broader concepts of this invention.

The following examples illustrate the best mode now contemplated of carrying out this invention, including specific embodiments. The invention is not limited to these specific embodiments. In these examples all percentages are by weight unless otherwise indicated, all parts by weight are indicated by $w$, all parts by volume are indicated by $v$ and each part by weight ($w$) bears the same relationship to each part by volume (v) as the kilogram does to the liter.

EXAMPLE 1

This example illustrates the preparation of the zinc (II) chelate of 1,1,5,5-tetramethyldithiobiuret.

A mixture of potassium thiocyanate (20.0 w) and acetone (250 v) is stirred until the potassium thiocyanate is dissolved and then dimethylthiocarbamoyl chloride (24.7 w) is added. The mixture is heated at reflux for 20 minutes, cooled to 25°C. and anhydrous dimethylamine (9.0 w) is passed slowly into the reaction mixture with cooling so that the temperature is maintained at less than 30°C. during this addition and for an additional 10 minutes. The reaction mixture is then heated to 40°–50°C. for 10 minutes. The mixture is cooled to 25°C. and aspirated for 5 minutes to remove unreacted dimethylamine. The mixture is then further cooled to less than 10°C. and the potassium chloride which forms during the reaction is removed by filtration. The potassium chloride is washed with acetone and the wash is combined with the filtrate. Acetone is added to the filtrate to bring the total volume up to 300 v.

This acetone solution containing 1,1,5,5-tetramethyldithiobiuret is stirred and a solution of zinc chloride (10.9 w) dissolved in distilled water (50 v) is added dropwise. After one hour, cold distilled water (800 v) is added. Typically an oil separates which gradually solidifies. The resulting solid is then filtered, washed on the filter with water and air-dried. The solid is triturated with warm ethanol and filtered. The resulting solid is then recrystallized twice from benzene. Typically the product (8.0 w) is in the form of white powder crystals which have a melting point of 202°–204°C. These crystals consist essentially of zinc (II) chelate of 1,1,5,5-tetramethyl dithiobiuret.

Typical analysis of this product shows N = 18.6%, S = 28.7% and Zn (by atomic absorption) = 14.8% and Zn (by ethylene diamine tetraacetic acid titration) = 14.5%. The calculated analysis for the zinc (II) chelate of 1,1,5,5-tetramethyldithiobiuret is N = 18.8%, S = 28.7% and Zn = 14.65%. Typically the NMR spectrum (in $CDCl_3$) of the product reveals a single sharp proton signal at 3.27 ppm. which indicates that all the protons are equivalent. The UV spectrum (in $CH_2Cl_2$) has a maximum at 273 nm. ($\alpha$64.5) and a minimum of 241 nm. ($\alpha$49.5). Polarographic results also indicate that this compound is a chelated salt and not an ionic salt.

EXAMPLE 2

This example illustrates the preparation of the zinc (II) chelate of 1,1,5,5-tetramethyldithiobiuret by a procedure which includes isolating the intermediate 1,1,5,5-tetramethyldithiobiuret.

The procedure of Example 1 is repeated until after the dimethylamine addition and the following heating period. The reaction mixture is cooled to 25°C. and is poured into 600 v of cold water, acidified with concentrated hydrochloric acid and twice extracted with methylene chloride. The extract is dried over sodium methylene sulfate and the solvent is removed on a rotary evaporator at 50°C. during 15–20 minutes. The tan, solid residue is recrystallized from 100% ethanol to give a light tan crystalline product. Residual ethanol is removed on a rotary evaporator. Typically light tan crystals melting at 113°–115°C. are obtained. This product (21.5 w) consists essentially of 1,1,5,5-tetramethyldithiobiuret.

The product is stored in a dark bottle under nitrogen in a cool place until ready for use.

A portion (19.1 w) of the 1,1,5,5-tetramethyldithiobiuret product is dissolved in acetone (250 v). The solution is stirred magnetically and a solution of zinc chloride (6.15 w) dissolved in distilled water (15 v) is added dropwise. Typically after about 1.5 hours a solid begins to separate. Stirring is discontinued after 2 hours and the reaction proceeds for an additional 12 hours. Distilled water is added slowly with stirring. A white solid which remains undissolved is filtered and recrystallized from benzene and then air-dried. Typically a white powder (9.5 w) having a melting point of 202°–204°C. is obtained.

EXAMPLE 3

This example illustrates the preparation of the Ni (II) chelate of 1,1,5,5-tetramethyldithiobiuret.

The nickel (II) chelate of 1,1,5,5-tetramethyldithiobiuret is prepared using the procedure described in Example 1 using nickel chloride instead of the zinc chloride. Typically a gray purple colored solid is obtained. Elemental analysis of this product indicates N = 18.9% and S = 28.8%. The calculated analysis for Ni (II) chelate of 1,1,5,5-tetramethyldithiobiuret is N = 19.15% and S = 29.2%.

EXAMPLE 4

This example illustrates the tin (II) chelate of 1,1,5,5-tetramethyldithiobiuret.

The tin (II) chelate of 1,1,5,5-tetramethyldithiobiuret is prepared by the procedure described in Example 1 using stannous chloride instead of zinc chloride. Typically a yellow powder melting at 230°–234°C. is obtained.

EXAMPLE 5

This example illustrates the preparation of the copper (I) chelate of 1,1,5,5-tetramethyldithiobiuret.

The 1,1,5,5-tetramethyldithiobiuret is prepared and isolated as in Example 2. A portion (19.1 w) of the isolated product is dissolved in acetone (250 v) and a solution of cupric chloride (5.4 w) dissolved in water (10 v) is added dropwise to the 1,1,5,5-tetramethyldithiobiuret-acetone solution. Typically a solid product consisting essentially of a mixture of 3,5-bis(dimethylamino)-1,2,4-dithiazolium chloride and the copper (I) chelate of 1,1,5,5-tetramethyldithiobiuret starts to form immediately. The reaction is continued at room temperature for 12 hours and the separated solid product is filtered. The solids are washed with distilled water to separate the water-soluble dithiazolium chloride from the water-insoluble copper (I) chelate. After air-drying a yellow solid product (7.08 w) is obtained. Typically the analysis of this product shows N = 14.7% and S = 22.5%. The calculated analysis for the Cu (I) chelate 1,1,5,5-tetramethyldithiobiuret (for the dihydrate) is N = 14.5% and S = 22.2%.

EXAMPLE 6

This example illustrates the preparation of the mercury (II) chelate of 1,1,5,5-tetraethyldithiobiuret.

1,1,5,5-Tetraethyldithiobiuret is prepared using the procedure of Example 1 and the following reagents:

| | |
|---|---|
| potassium thiocyanate | 10.0 w |
| acetone | 125 v |
| diethylthiocarbamoyl chloride | 15.15 w | diethylamine                7.3 w

The resulting product is not isolated and after the KCl has been removed by filtration a solution of mercuric acetate (8.0 w) dissolved in water (50 v) is added dropwise to the solution of the 1,1,5,5-tetraethyldithiobiuret. A yellow solid separates and after 24 hours the solid is filtered. The resulting solid is triturated with methanol and then hexane. Typically, after air drying, a light tan crystalline solid (17.03 w) having a melting point of 109°–112°C. is obtained.

Typically the analysis of the product shows N = 12.3%, S = 18.7% and Hg = 29.3%. The calculated analysis for the mercury (II) chelate of 1,1,5,5-tetraethyldithiobiuret is N = 12.2%, S = 18.5% and Hg = 29.0%.

EXAMPLE 7

This example illustrates the preparation of the nickel (II) chelate of 1,1,5,5-tetraethyldithiobiuret.

An acetone solution of 1,1,5,5-tetraethyldithiobiuret is generated in situ as described in Example 6. A solution of nickel (II) acetate (8.8 w) dissolved in water (100 v) is added dropwise to the solution. Typically after air drying, a dull purple colored powder which melts at 156°–157°C. is isolated. The product is soluble in benzene and insoluble in water.

The analysis of this solid product is N = 15.4%, S = 24.0% and Ni = 10.1%. The calculated analysis for the Ni (II) chelate of 1,1,5,5-tetraethyldithiobiuret is N = 15.2%, S = 23.2% and Ni = 10.7%.

EXAMPLE 8

This example illustrates the preparation of the zinc (II) chelate of 1,1,5,5-tetraethyldithiobiuret.

The procedure described in Example 6 is repeated using zinc (II) acetate and an in situ generated acetone solution of 1,1,5,5-tetraethyldithiobiuret. The solid product is purified by recrystallization from 100% ethanol. Typically an off-white crystalline product is obtained having a melting point of 115°–118°C.

The analysis of this product is N = 15.0%, S = 22.9% and Zn = 10.7%. The calculated analysis for the Zn (II) chelate of 1,1,5,5-tetraethyldithiobiuret is N = 15.1%, S = 23.0% and Zn = 11.7%.

EXAMPLE 9

This example illustrates the preparation of the sodium salt of 1,1,5,5-tetramethyldithiobiuret.

A solution of sodium methoxide in methanol is prepared by diluting 25% NaOCH$_3$ (54.0 w) in methanol with methanol (250 v). 1,1,5,5-Tetramethyldithiobiuret (48.0 w) is added in portions while the solution is stirred. The stirring is continued for 30 minutes. The solvent is removed on a rotary evaporator at 50°C. The residue, which typically is a tan solid, is stirred with CH$_2$Cl$_2$ (100 v) to remove unreacted dithiobiuret. The solvent is removed by drying on a rotary evaporator. Typically a water-soluble white powder (44.7 g.) having a melting point of 219°–221°C. is obtained.

An aqueous solution of this product is acidified by the addition of concentrated HCl. Typically a white solid is obtained having a melting point identical to that of the starting 1,1,5,5-tetramethyldithiobiuret. The infrared spectrum of the acidification product also indicates that 1,1,5,5-tetramethyldithiobiuret is regenerated.

To a solution of the original product (4.26 w) in water (25.0 v) is added a solution of zinc chloride (1.0 w) in water (5 v). A white solid product is obtained having properties identical to the product of Example 1.

EXAMPLE 10

This example illustrates the preparation of the sodium salt of 1,3-bis(N-morpholino)-1,3-dithiono-2-azapropane.

A solution of sodium methoxide in methanol is prepared by diluting 25% NaOCH$_3$ (13.4 w) in methanol with methanol (100 v). 1,3-bis(N-morpholino)-1,3-dithiono-2-azapropane (17.4 w) is added to the solution in small portions. Additional methanol (75 v) is added to obtain a solution. After 15 minutes the solution is filtered and methanol is removed from the filtrate using a rotary evaporator. The residue is stirred with dichloromethane (75 v) for 10 minutes. The resulting mixture is filtered and the solid product is dried using a rotary evaporator. Typically a light tan product (20.6 w) having a melting point of 205°–210°C. is obtained.

As stated above, the metal derivatives of 1,1,5,5-tetrasubstituted dithiobiurets of this invention are biologically active compounds. Some of the varied biological activities of these compounds are illustrated by the following test data. The most important, advantageous biological activity of these compounds appears to be their activity as a population control agent for insects, acarids, animals and humans. The expression "population control agent" is used herein to mean an agent that inhibits reproduction in treated members of the population. When applied to mammals the expression includes contraception agents and pregnancy terminators. In the case of insects it refers to chemosterilants and metamorphosis inhibitors that prevent maturation of the insect into the adult stage. Certain of the compounds of this invention are animal contraceptives which are effective when either the male or female is treated for a period of time prior to mating. The compounds have other useful biological properties. When orally administered to male mammals the compounds of this invention inhibit the growth of, or reduce the size of, the prostate gland. Thus, they can be used in treating prostatic hypertrophy.

Evaluation as Animal Contraceptives

The zinc (II) chelate of 1,1,5,5-tetramethyldithiobiuret was evaluated as an animal contraceptive by the treatment of male and/or female rats prior to mating. Separate unmated female and/or male rats were fed a diet to which had been added the test compound at 1–5 mg./kg. dosage levels for seven days before mating. After the 7-day test period the animals were cohabitated to mate. After mating, the females were separated and observed through a period of time equal to the normal gestation period for rats. Their litters were compared with that of a control group of animals who had the same diet but without the zinc (II) chelate of 1,1,5,5-tetramethyldithiobiuret. At the dosage levels of 1–5 mg./kg. no pregnancies resulted.

Evaluation as Animal Pregnancy Terminators

Pregnant rats were treated with the test compounds at selected times and concentrations during the gestation period. After treatment, the animals were observed for abortions and were sacrificed and examined for the number and normality of their implants. The zinc (II), tin (II) and copper (I) chelates of 1,1,5,5-tetramethyldithiobiuret were evaluated in these tests. At a dosage level of 1–5 mg/kg. the zinc (II) chelate resulted in complete resorption of the embryos or abortion of the fetuses, depending upon what time during the gestation period treatment was made. The tin (II) chelate was 100% effective as a pregnancy terminator but at the high dosage level of 50–100 mg./kg. The copper (I) chelate was 100% effective as a pregnancy terminator at a dosage level of 10 mg./kg.

Evaluation as Insect Chemosterilant

Unmated housefly adults were held in screen cages with 15 males and 15 females in each cage. The compound to be tested as a chemosterilant was formulated as an emulsion or solution and added to the water source in each cage at the selected concentration. After four or five days a plastic cup of milk-soaked cotton was pressed against the screen bottom of the cage to serve as an egg-laying substrate. After 48 hours this was removed and examined for the presence of eggs. In the case where eggs had been deposited in the plastic cups, these cups were held for 48 hours for egg hatch determination. A control group of unmated housefly adults was kept in separate cages and was not treated with the test compound. The quantity of eggs laid and the percent hatch are compared for the flies treated with selected concentrations of the zinc (II) chelate of 1,1,5,5-tetramethyldithiobiuret and for the control group in the following Table 1.

TABLE 1

| Concentration | Egg Deposited at[a] | % Egg Hatch |
| --- | --- | --- |
| 0.05% | 0 | 0 |
| 0.01% | 0 | 0 |
| 0.005% | 0 | 0 |
| Untreated | 10 | 100 |

[a] Estimated on a 0–10 scale, with 10 being the average for untreated flies.

Evaluation as Inhibitor of Metamorphosis of Insects

Ten larvae of the yellow fever mosquito in the fourth and last larval instar were placed in solutions, suspensions or emulsions containing chosen concentrations of the compound under test. The mosquitoes were held through the pupal and adult stages to determine the mortalities of pupae and partially emerged adults. The results when the larvae were treated with the specified concentrations of the zinc (II) chelate of 1,1,5,5-tetramethyldithiobiuret are shown in the following Table 2.

TABLE 2

| Concentration (in ppm) | Number Treated | % Dead Larvae | % Dead Pupa | % Normal Adults |
| --- | --- | --- | --- | --- |
| 5 | 10 | 100 | 0 | 0 |
| 0.5 | | 40 | 50 | 10 |
| 0.25 | | 30 | 30 | 40 |
| 0.1 | | 0 | 40 | 60 |

Evaluation as Plant Defoliant

The test compounds were formulated with 4.0% of a surfactant, (a blend of polyoxyethylene (20%) sorbitan monooleate in which the oxyethylene content is about 20 mole percent, with mono- and di-glycerides of fat-forming fatty acids and an antioxidant mixture), 5% cyclohexanone, 15% acetone and water and sprayed at the rates indicated in the following Table 3 on four-week old cotton plants. Ten days after treatment a count is made of the number of abcissed and desiccated leaves on each plant. The percent leaf abscission and/or desiccation was calculated for each plant. The compounds tested were (A) the zinc (II) chelate of 1,1,5,5-tetramethyldithiobiuret of this invention and (B) 3,5-bis(dimethylamino)1,2,4-dithiazolium chloride of U.S. Pat. No. 3,166,564. The results are shown in the following Table 3.

TABLE 3

| | Rate (lb./A) | % Abscission | % Desiccation |
| --- | --- | --- | --- |
| Compound A | 1.25 | 35 | 35 |
| | 2.5 | 52 | 22 |
| | 5.0 | 56 | 28 |
| | 10.0 | 54 | 26 |
| Compound B | 1.25 | 70 | 11 |
| | 2.5 | 76 | 16 |
| | 5.0 | 77 | 16 |
| | 10.0 | 93 | 7 |

To use the compounds of this invention as population control agents for mammals, including humans, they generally are administered in combination with conventional liquid or solid vehicles to provide elixirs, suspensions, tablets, capsules, powders and the like, according to conventional pharmaceutical practice.

Other features, advantages and specific embodiments of this invention will become readily apparent to those exercising oridinary skill in the art after reading the foregoing disclosures. Such specific embodiments are within the scope of the claimed subject matter unless expressly indicated to the contrary by claim language. Moreover, while specific embodiments of this invention have been described in considerable detail, variations and modifications of them can be effected without departing from the spirit and scope of the invention as disclosed and claimed.

The expression "consisting essentially of" as used in this specification excludes any unrecited substance at a concentration sufficient to substantially adversely affect the essential properties and characteristics of the composition being defined, while permitting the presence of one or more unrecited substances at concentrations insufficient to substantially adversely affect said essential properties and characteristics.

What I claim and desire to protect by letters Patent is:

1. A metal salt of a 1,1,5,5-tetrasubstituted dithiobiuret of the formula:

in which $R^1$, $R^2$, $R^3$ and $R^4$ independently of each other are selected from the group consisting of $C_1$-$C_{18}$ alkyl, $C_6$-$C_{12}$ aryl, $C_3$-$C_{12}$ cycloalkyl and these radicals substituted by at least one member of the group consisting of hydroxyl, $C_1$-$C_4$ alkyl, $C_1$-$C_8$ aryl, halo and nitro.

2. A compound according to claim 1 in which $R^1$, $R^2$, $R^3$ and $R^4$ are each methyl, and the metal of said metal salt is selected from the group consisting of the alkali metals, the alkaline earth metals, zinc, cadmium, tin, mercury, copper, nickel, chromium, iron, silver, manganese, and beryllium.

3. A compound according to claim 1 in which $R^1$, $R^2$, $R^3$ and $R^4$ are each ethyl.

4. A compound according to claim 1 in which the metal is zinc.

5. A compound according to claim 1 in which the metal is sodium.

6. A compound according to claim 1 in which the metal is copper.

7. The zinc salt of 1,1,5,5-tetramethyldithiobiuret.

* * * * *